US012766724B2

(12) United States Patent
Fang et al.

(10) Patent No.: US 12,766,724 B2
(45) Date of Patent: Oct. 20, 2026

(54) MACHINE AND SYSTEM FOR DETERMINING ABNORMALITY OF MACHINE POSTURE

(71) Applicant: Point Robotics Medtech Inc., Hsinchu County (TW)

(72) Inventors: Ting-Yun Fang, Hsinchu County (TW); Ting-Jen Yeh, Hsinchu County (TW)

(73) Assignee: Point Robotics Medtech Inc., Hsinchu County (TW)

( * ) Notice: Subject to any disclaimer, the term of this patent is extended or adjusted under 35 U.S.C. 154(b) by 196 days.

(21) Appl. No.: 18/508,247

(22) Filed: Nov. 14, 2023

(65) Prior Publication Data

US 2024/0342910 A1 Oct. 17, 2024

(30) Foreign Application Priority Data

Apr. 14, 2023 (TW) ................................ 112114070

(51) Int. Cl.
*A61B 34/20* (2016.01)
*A61B 34/30* (2016.01)
(Continued)

(52) U.S. Cl.
CPC ............ *B25J 9/1674* (2013.01); *A61B 34/20* (2016.02); *A61B 34/30* (2016.02); *A61B 90/39* (2016.02);
(Continued)

(58) Field of Classification Search
CPC ...... B25J 9/1674; B25J 9/1607; B25J 9/1697; B25J 9/1664; A61B 34/20; A61B 34/30;
(Continued)

(56) References Cited

U.S. PATENT DOCUMENTS 9,827,054 B2 11/2017 Richmond et al.
2003/0055410 A1* 3/2003 Evans .................. A61B 34/35
606/1

(Continued)

FOREIGN PATENT DOCUMENTS

CN 113490464 A 10/2021
CN 114952855 A 8/2022

OTHER PUBLICATIONS

Search Report issued on Jun. 6, 2024 for EP application No. 23218569.4.

*Primary Examiner* — Jason Holloway

(74) *Attorney, Agent, or Firm* — Li & Cai Intellectual Property Office

(57) ABSTRACT

A machine posture inspection method and a machine posture inspection system are provided. The method includes: configuring an image capturing device to capture a current image of a region where a machine device is located, and configuring a processing device to: identify a reference marker in the current image and a first marker connected to the machine device; and calculate and obtain a current posture of the machine device according to the reference marker and the first marker; configure a motor encoder to measure an encoder signal associated with a motor; and determining whether or not the machine device is abnormal according to the current posture and the encoder signal.

10 Claims, 8 Drawing Sheets

(51) Int. Cl.
*A61B 90/00* (2016.01)
*B25J 9/16* (2006.01)

(52) U.S. Cl.
CPC ........... *B25J 9/1607* (2013.01); *B25J 9/1697* (2013.01); *A61B 2034/2065* (2016.02); *A61B 2034/2068* (2016.02); *A61B 2090/3983* (2016.02)

(58) Field of Classification Search
CPC ............ A61B 90/39; A61B 2034/2065; A61B 2034/2068; A61B 2090/3983
See application file for complete search history.

(56) References Cited

U.S. PATENT DOCUMENTS

| | | | | |
|---|---|---|---|---|
| 2009/0326556 | A1* | 12/2009 | Diolaiti | A61B 1/00149 606/130 |
| 2014/0228862 | A1* | 8/2014 | Inoue | A61B 34/37 606/130 |
| 2017/0143429 | A1* | 5/2017 | Richmond | A61B 34/37 |
| 2017/0243339 | A1* | 8/2017 | Yamamoto | G01N 21/8851 |
| 2020/0121403 | A1* | 4/2020 | Awano | A61B 34/20 |

* cited by examiner

MACHINE AND SYSTEM FOR DETERMINING ABNORMALITY OF MACHINE POSTURE

CROSS-REFERENCE TO RELATED PATENT APPLICATION

This application claims the benefit of priority to Taiwan Patent Application No. 112114070, filed on Apr. 14, 2023. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to an inspection method and an inspection system, and more particularly to a machine posture inspection method and a machine posture inspection system.

BACKGROUND OF THE DISCLOSURE

In conventional technology for controlling a robotic arm, a 3D camera is often used to measure positions of a fixed end and a moving end of a machine, as well as a position of an object. Then, a coordinate transformation is performed to calculate a posture of the robotic arm and a target for the robotic arm to move to. Furthermore, based on inverse kinematics, a speed command or a brake position command for the robotic arm can be derived from a target point in space, and these commands are transmitted to a controller by a computer to practically conduct navigation through controlling the brake. By repeating the above steps in a closed loop manner, the robotic arm can immediately and continuously move to the target, thereby reducing navigation errors.

However, in conventional control technology, the ability for monitoring the robotic arm is finite, as some abnormalities (such as, marker falling, robot mechanism malfunction, motor abnormality, encoder abnormality, and failure of the controller caused by excessive external force) occur imperceptibly, a position of the robotic arm may be erroneously determined, thereby resulting in abnormal movement of the robotic arm.

SUMMARY OF THE DISCLOSURE

In response to the above-referenced technical inadequacies, the present disclosure provides a machine posture inspection method and a machine posture inspection system capable of ensuring a normal machine posture.

In one aspect, the present disclosure provides a machine posture inspection method, which includes: configuring an image capturing device to capture a current image of a region where a machine device is located; and configuring a processing device to: identify a reference marker in the current image and a first marker associated with the machine device; and calculate and obtain a current posture of the machine device according to the reference marker and the first marker; configure at least one motor encoder to measure an encoder signal associated with the at least one motor; and determine, according to the current posture and the encoder signal, whether or not the machine device is abnormal.

In another aspect, the present disclosure provides a machine posture inspection system, which includes a machine device, an image capturing device and a processing device. The machine device includes at least one motor and at least one motor encoder. The image capturing device is configured to capture a current image of a region where a machine device is located. The processing device is electrically connected to the image capturing device and the machine device, wherein the processing device is configured to: identify a reference marker in the current image and a first marker associated with the machine device; calculate and obtain a current posture of the machine device according to the reference marker and the first marker; measure an encoder signal associated with the at least one motor through the at least one motor encoder; and determine, according to the current posture and the encoder signal, whether or not the machine device is abnormal.

Therefore, in the machine posture inspection method and machine posture inspection system provided by the present disclosure, a 3D image capturing device and a motor encoder are utilized to detect and obtain a posture of the machine device and a motor posture, which are compared with each other to ensure that the posture and movement of the machine device is normal. When an abnormality is detected, a warning is issued, and the machine device is stopped to ensure system safety.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
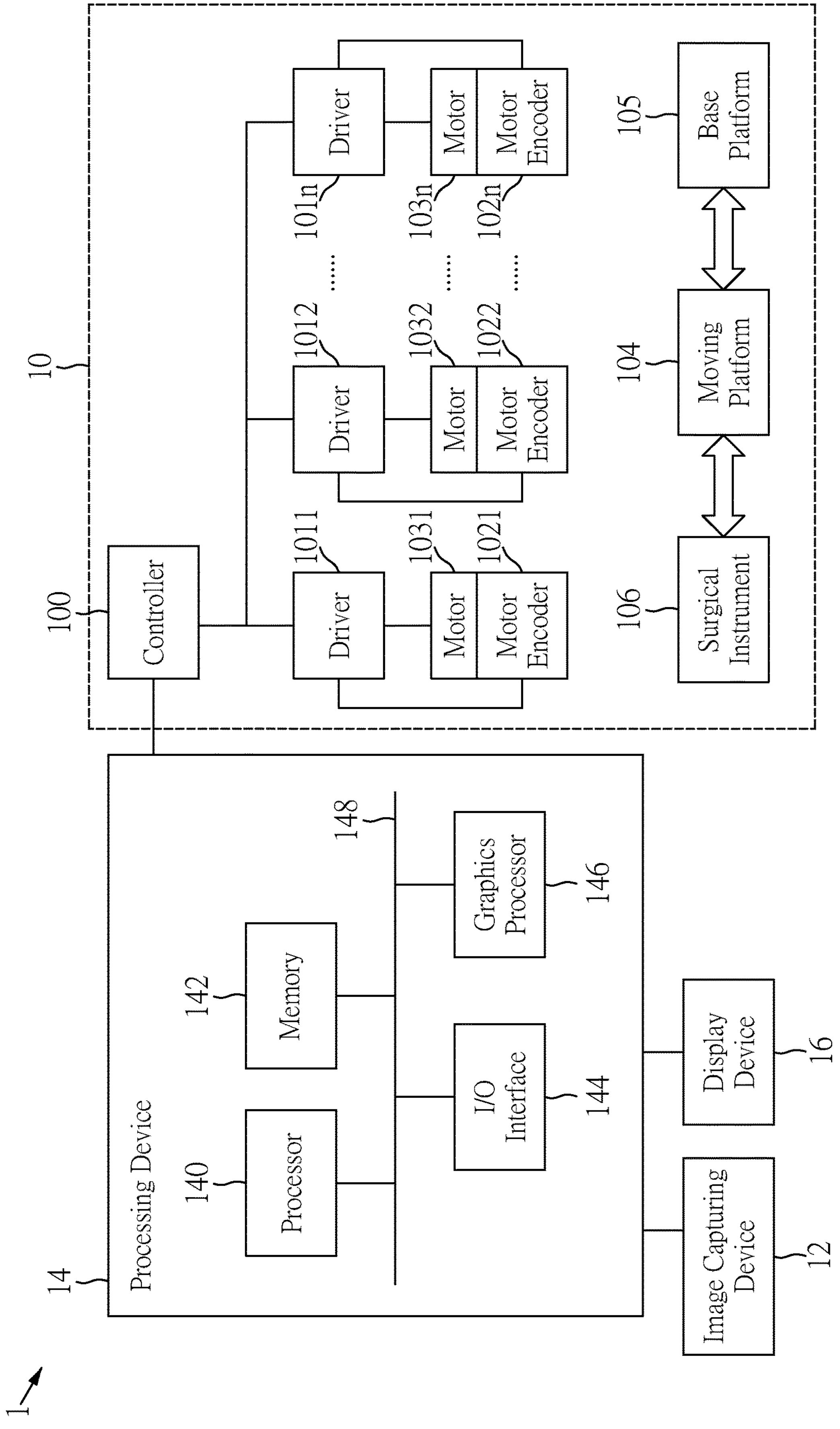
FIG. 1 is a functional block diagram of a machine posture inspection system according to one embodiment of the present disclosure.

FIG. 1 is a functional block diagram of a machine posture inspection system according to one embodiment of the present disclosure.

Reference is made to FIG. 1, which illustrates a machine posture inspection system 1 in one embodiment of the present disclosure, and the system 1 includes a machine device 10, an image capturing device 12, a processing device 14 and a display device 16.

The processing device 14 includes a processor 140, a memory 142, an input/output (I/O) interface 144 and a graphics processor 146. The processing device 14 can be implemented by, for example, a database, a general processor, a computer, a server, other unique hardware devices with specific logic circuits or devices with specific functions, such as unique hardware integrating program codes and processors/chips. More specifically, part or all of the inspection system and inspection method provided by the present disclosure can be implemented using computer programs, and the computer programs can be stored in a non-transitory computer-readable recording medium, such as a read-only memory, a flash memory, a floppy disk, a hard disk, an optical disk, a portable storage drive, a magnetic tape, a database that can be accessed through the internet, or computer-readable recording media with the same function that can be easily conceived by those skilled in the art.

The processor 140 can be, for example, a programmable logic controller circuit, a micro-processor circuit, an integrated circuit of a micro-control circuit, or a central processing unit.

The memory 142 is any storage device that can be used to store data, such as, but not limited to, a random access memory (RAM), a read only memory (ROM), a flash memory, a hard disk or other storage device that can be used to store data.

The graphic processor 146 can also be referred to as a display core, a visual processor, a display chip, a display card, or a graphics chip, which can be a microprocessor that performs graphics operations in a personal computer, workstation, game console, or a mobile device (such as a tablet computer or a smart phone). The processor 140, the memory 142, the I/O interface 144 and the image processor 146 can communicate through a bus 148, but the present disclosure is not limited thereto.

In addition, in one embodiment of the present disclosure, the I/O interface 144 can include one or more physical connection ports (for example, it can be a general-purpose input/output interface or an interface that supports HDMI, DisplayPort, USB, Ethernet, Ethernet for control automation technology (EtherCAT) and other specifications) and one or more wireless communication modules (such as wireless communication interface cards supporting Bluetooth, WI-FI and other specifications), and the processing device 14 can be electrically connected to the machine device 10, the image capturing device 12 and the display device 16 through the I/O interface 144 in a wired or wireless manner.

Further, the image capturing device 12 can be, for example, a three-dimensional camera device including a plurality of cameras, and can be configured to capture a current image of a region where the machine device 10 is located. The image capturing device 12 can capture and measure depth information of an object. The camera device can capture the depth information of the object and the environment in different ways, such as by using a depth sensor, a stereo camera, or a time-of-flight technology, so as to obtain a precise position of the object.

The machine device 10 can be, for example, a parallel robot, which can include a controller 100, drivers 1011, 1012 . . . **101*n*, motor encoders 1021, 1022 . . . , 102*n* and motors 1031, 1032 . . . 103*n*. The machine device 10 can be a parallel robot, for example, a surgical instrument based on a Stewart platform, and the machine device 10 includes a base platform 105 and a mobile platform 104. The mobile platform 104 has a plurality of degrees of freedom relative to the base platform 105, and is driven by the motors. The mobile platform 104 can grip a surgical instrument 106** such as a drill, a trocar, or a saw blade through an adapter.

In detail, a driving mechanism of the machine device 10 can, for example, adopt a parallel mechanism with six degrees of freedom of movement. Within the driving mechanism, a total of six actuating units and corresponding six limbs are provided. Each actuating unit can include a motor, a coupling, a lead screw, and a slide rod. The controller 100 can be electrically connected to the drivers 1011, 1012 . . . , and **101*n*, so as to drive the motors 1031, 1032 . . . , and 103*n* according to control commands of the controller 100, which further rotates the lead screws to cause the limbs to move. In addition, the drivers 1011, 1012 . . . , 101*n* can be respectively in electric connection with the motor encoders 1021, 1022 . . . , 102*n*, so as to receive encoder signals when the motors 1031, 1032 . . . , 103*n* are driven, such that position information of the motors 1031, 1032 . . . , and 103*n* can be obtained and sent to the controller 100 as position feedback signals. In addition, the processing device 14 can also be directly or indirectly in electric connection with the motor encoders 1021, 1022 . . . , 102*n*, so as to obtain the encoder signals of the motor encoders 1021, 1022 . . . , 102*n***.

Through the above configuration, when the actuating unit drives the limb to move, the mobile platform 104 is moved or rotated to different positions/orientations in space, thereby moving the surgical instrument on the adapter to a desired position/orientation. The above-mentioned parallel mechanism utilizes the familiar Stewart platform, and thus details thereof are omitted herein. Furthermore, in addition to the above-mentioned parallel robot, the machine device 10 may also be a serial robot.

Figure 2:
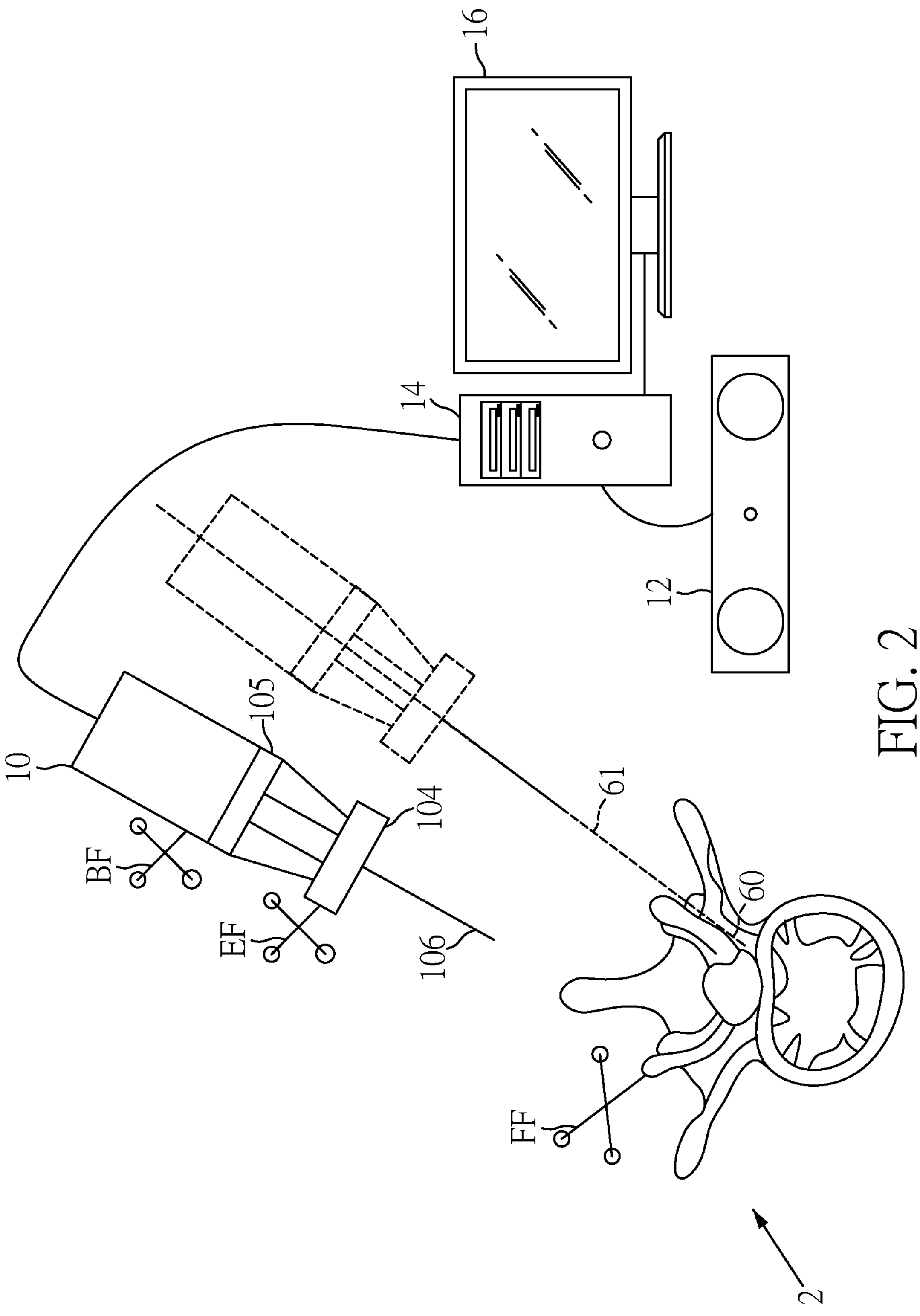
FIG. 2 is a schematic diagram of a machine device being used to perform a surgery in a surgical environment according to one embodiment of the present disclosure.

FIG. 2 is a schematic diagram of a machine device being used to perform a surgery in a surgical environment according to one embodiment of the present disclosure. Reference is made to FIG. 2. A reference marker BF, such as a robotic base frame, can be fixedly arranged on the base platform 105, and a first marker EF, such as an end effector frame, can be fixedly arranged on the mobile platform 104. The reference marker BF and the first marker EF can assist in detecting orientations and positions of the machine device 10 and the surgical instrument 106 relative to a surgical site 2, for example, by any conventional positioning methods such as optical positioning, electromagnetic positioning, or inertial positioning. In addition, the reference marker BF and the first marker EF can include a plurality of markers for emitting electromagnetic signals, sound waves, heat or other sensible signals, and can be installed on the base platform 105 and the mobile platform 104 in specific orientations and angles relative to the surgical instrument 106. However, in one embodiment of the present disclosure, the optical positioning method can be adopted; therefore, the reference marker BF and the first marker EF can each include one or more marker balls. In one preferred embodiment of the present disclosure, the reference marker BF and the first marker EF are reflective balls, respectively disposed on the base platform 105 and the mobile platform 104, or marking devices that actively generate sensible signals. Moreover, a plurality of detection markers can also be arranged near the surgical site 2 (for example, a dynamic reference frame implanted near the surgical site 2), such that the processing device 14 can detect the position and the orientation of the surgical instrument 106 relative to the surgical site 2 through the image capturing device 12 or other optical sensors.

As further shown in FIG. 2, in a surgical environment, a surgery can be performed on the surgical site 2 by an operator holding the machine device 10 (e.g., a robotic arm). The processing device 14 can be configured to receive relevant position information of the machine device 10 from the image capturing device 12, and then use the machine device 10 to guide movement of the surgical instrument 106 according to the position information.

In more detail, a second marker FF can be arranged near the surgical site 2 (for example, a dynamic reference frame pre-implanted near the surgical site 2), and the processing device 14 can obtain an image of the second marker FF near the surgical site 2 through an optical detector (for example, the image capturing device 12). Further on, pre-acquired tomographic images are synthesized to establish a three-dimensional virtual model of the surgical site 2 and internal bones, and detected positions of the markers are labeled in the virtual model. The established 3D virtual model can be processed and rendered by the graphic processor 146, and then displayed on a navigation interface shown on the display device 16.

In more detail, for the markers arranged near the surgical site 2 (such as the aforementioned dynamic reference frame), after registering spatial coordinates of the markers in the real space to coordinates of the markers in the virtual space containing medical images, a spatial coordinate transformation matrix can be obtained. The processing device 14 can further utilize the spatial coordinate transformation matrix, the image capturing device 12 can capture the dynamic reference frame near the surgical site 2, and then the surgical instrument 106, the three-dimensional virtual model of the surgical site 2 and the internal skeleton are processed and rendered by the graphics processor 146 and displayed on the navigation interface shown on the display device 16.

Then, the user can plan a surgical path 60 to be performed in the three-dimensional virtual model displayed on the display device 16 (for example, the surgical path is defined according to one or more pedicle screws to be implanted in the surgical site). Moreover, after the surgical path 60 is planned, the processing device 14 can further calculate and generate a virtual axis 61 extending outward of epidermis over the surgical site based on the surgical path 60, and display the virtual axis 61 on the navigation interface to indicate a surgical location for the user, thereby assisting the user to steadily move the surgical instrument along the surgical path 60 during the operation.

The machine posture inspection method provided by the present disclosure is further described below, the machine posture inspection method is applicable to the above machine posture inspection system 1, but the present disclosure is not limited thereto.

Figure 3:
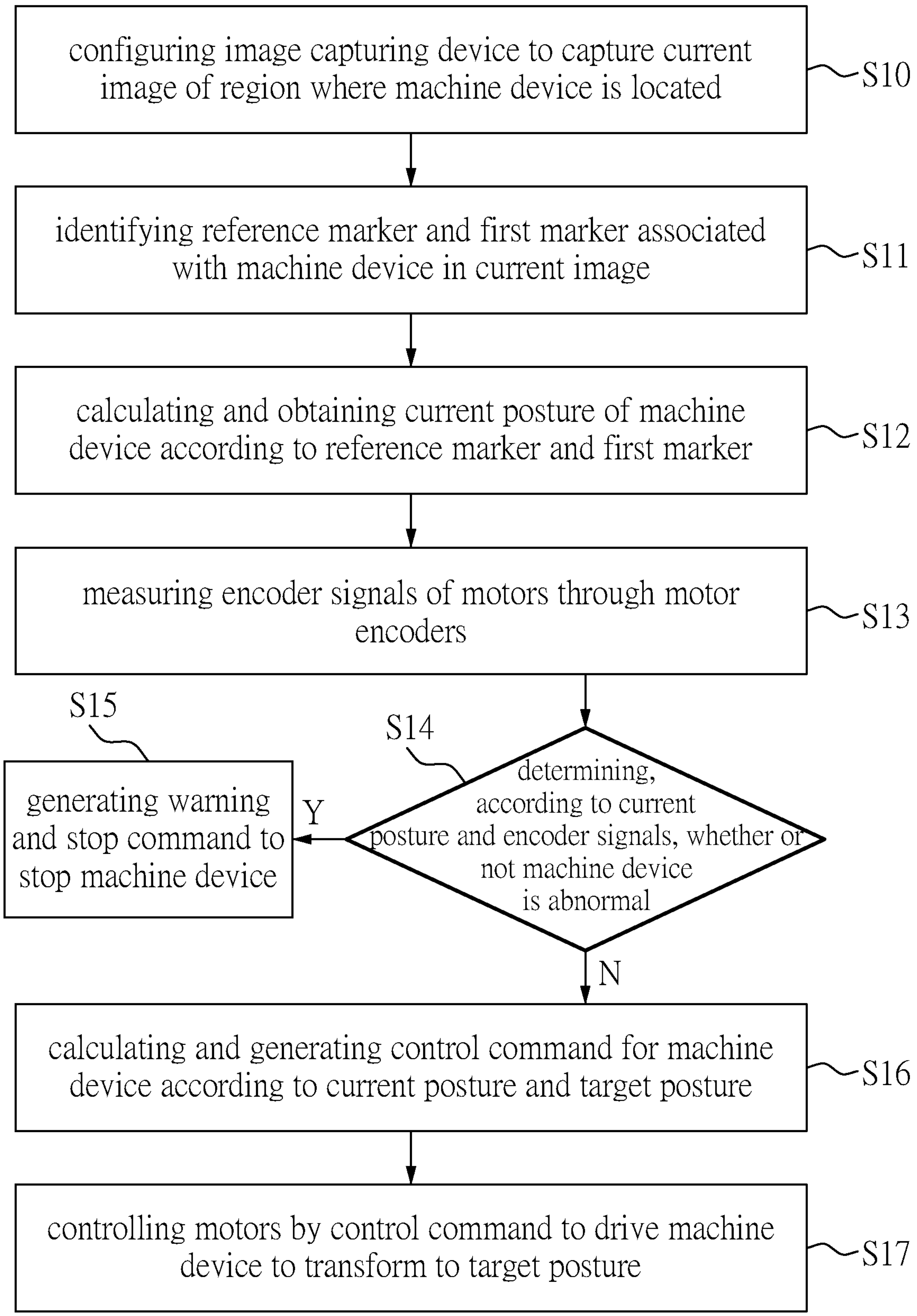
FIG. 3 is a flowchart of a machine posture inspection method according to one embodiment of the present disclosure.

Reference is made to FIG. 3, which is a flowchart of a machine posture inspection method according to one embodiment of the present disclosure. As shown in FIG. 3, the inspection method includes the following steps:

Step S10: configuring the image capturing device to capture a current image of a region where the machine device is located. In this step, a three-dimensional camera device can be used to acquire images of the reference marker BF and the first marker EF fixed to the machine device 10 for subsequent determination of a posture of the mechanical device 10.

After the current image is obtained, the inspection method can further include configuring the processing device 14 to perform the following steps:

Step S11: identifying the reference marker and the first marker associated with the machine device in the current image. For example, the processor 140 can be configured to execute an object recognition algorithm to find the reference marker BF and the first marker EF in the current image; however, the present disclosure is not limited thereto. In some embodiments, the object recognition algorithm can be executed to find out the reference marker BF, the first marker EF and the second marker FF in the current image, and at the same time obtain the corresponding positions and orientations. Such information can be used to estimate the posture, the position and the orientation of the machine device 10, and the position and orientation of the surgical instrument 106 relative to the surgical site 2.

Step S12: calculating and obtaining a current posture of the machine device according to the reference marker and the first marker.

In detail, the mobile platform 104 and the base platform 105 can be rigid body platforms, respectively, and the rigid body platforms can build inertial coordinates and body coordinates for the Stewart platform mechanism constituted by the mobile platform 104 and the base platform 105. For example, a center of the base platform 105 can be used as an origin of the inertial coordinates, while the body coordinates are similar to the inertial coordinates, and an origin of the body coordinates is fixed at a center of the mobile platform 104. The inertial coordinates are fixed on the base platform 105 and non-movable, while the body coordinates move along with the mobile platform 104, which is the structure and coordinate definitions of the Stewart platform. Based on this coordinate definition, the position of the mobile platform 104 in space can be described by the inertial coordinates of the center of the mobile platform 104, and postures of the mobile platform 104 and the base platform 105 in space can be defined by a set of Euler angles.

In more detail, the position of the mobile platform 104 relative to the base platform 105 in space can be fully described by a transformation matrix, including six degrees of freedom of rotation and translation. The transformation matrix can be shown in the following equation:

$$T = \begin{bmatrix} R & P \\ 0 & 1 \end{bmatrix};$$

where T is the transformation matrix, R is a 3×3 rotation matrix, often described by Euler angles, and P is a 3×1 translation vector (x, y, z).

Therefore, since relative positions and orientation relationship between the reference marker BF and the base platform 105 are known, and relative positions and orientation relationship between the first marker EF and the mobile platform 104 are also known, the above-mentioned coordinate definition and the following equation can be used to estimate the current posture.

$$T_E^B = \left(T_{BF}^{tracker} T_B^{BF}\right)^{-1} T_{EF}^{tracker} T_E^{EF};$$

where $$T_E^B$$

is the current posture, $$T_{BF}^{tracker}$$

is position and orientation information of the reference marker BF, $$T_{B}^{BF}$$

is a transformation matrix for transforming the position and orientation information of the reference marker BF into position and orientation information of the base platform 105, $$T_{EF}^{tracker}$$

is position and orientation information of the first marker EF, $$T_{E}^{EF}$$

is a transformation matrix for transforming the position and orientation information of the first marker EF into position and orientation information of the mobile platform 104.

Step S13: measuring the encoder signals of the motors through the motor encoders.

As previously mentioned, the drivers 1011, 1012 . . . , 101*n* can receive the encoder signals when the motors 1031, 1032 . . . , 103*n* are driven, such that the position information of the motors 1031, 1032 . . . , and 103*n* can be obtained and sent to the controller 100 as the position feedback signals.

Step S14: determining, according to the current posture and the encoder signals, whether or not the machine device is abnormal.

Figure 4:
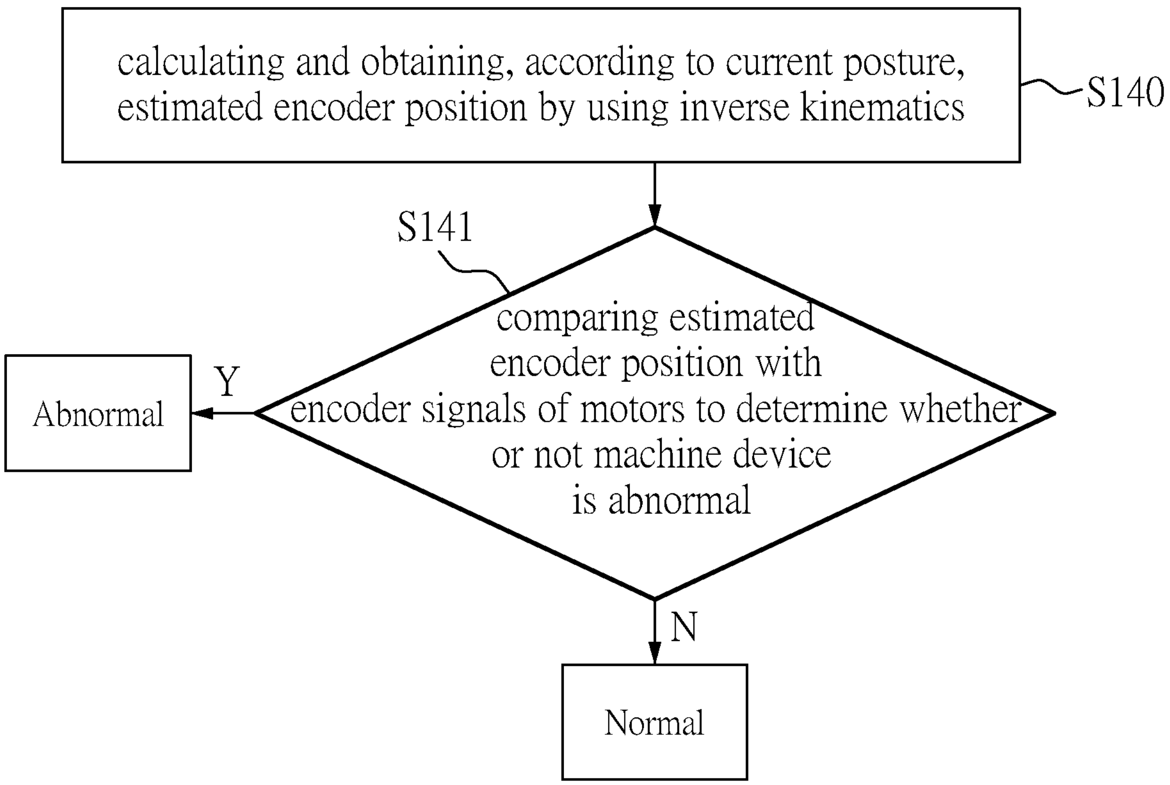
FIG. 4 is a first flowchart for step S14.

Reference is made to FIG. 4, which is a first detailed flowchart of step S14.

For example, when the machine device 10 is the parallel robot (such as the Stewart platform), the following steps can be performed:

Step S140: calculating and obtaining, according to the current posture, an estimated encoder position by using inverse kinematics.

In this step, according to the parallel robot architecture, the current posture $$(T_{E}^{B})$$

calculated and obtained in the previous steps can be used to calculate and obtain a posture of each motor through inverse kinematics. It should be understood, connection relationship among each motor and its corresponding brake shaft, the mobile platform 104 and the base platform 105 is known. Therefore, in a process of finding solutions through doing inverse kinematics, according to the postures of the mobile platform 104 and the base platform 105 in space, elongation or rotation of the brake shaft corresponding to each motor can be estimated as the posture of each motor, such that the estimated encoder position can be obtained.

Step S141: comparing the estimated encoder position with the encoder signals of the motors to determine whether or not the machine device is abnormal.

In one embodiment of the present disclosure, the motor encoder can be, for example, an incremental encoder, which can be decelerated by a mechanism to obtain an actual elongation or rotation of the brake shaft. For example, the robotic arm can be equipped with linear brakes, rotary brakes, or other brakes that surround a specific path (e.g., a cam), which can perform additional deceleration as needed. In this case, a final position of a working end of the brake can be obtained after changing the method for estimating the encoder position of the motor according to a form of the mechanism of the machine device 10.

In some embodiments of the present disclosure, a rotary motor can be used together with a ball screw to form a linear brake, and the position of a working end of the linear brake can be calculated and obtained according to the following equation:

$$\text{actuator length} = \text{encoder measurement} \times \frac{\text{Ball screw Lead (mm)}}{\text{encoder resolution}};$$

where actuator length is a length of the brake, encoder measurement is an original measurement value of the encoder, Ball screw Lead is an elongation of the ball screw, and encoder resolution is a resolution of the motor encoder.

Therefore, the actual elongation or rotation of the brake shaft can be further compared with the estimated elongation or rotation of the brake shaft to determine whether or not the machine device 10 is abnormal. When the actual elongation or rotation of the brake shaft is different from the estimated elongation or rotation of the brake shaft, it can be known that abnormalities, such as robot mechanism abnormalities, motor abnormalities, encoder abnormalities, or marker falling, may occur. On the contrary, the machine device 10 is normal. It should be noted that this step is conducted based on comparison between an estimated motor state and an actual motor state, but it is not limited to compare the estimated encoder position with the actual encoder position of the motor in the present disclosure. The estimated motor encoder signal can also be compared with the actual motor encoder signal. The transformation methods involving inverse kinematics, the motor posture, and the motor encoder signals are known to those skilled in the art, and thus details thereof will not be reiterated herein.

Figure 5:
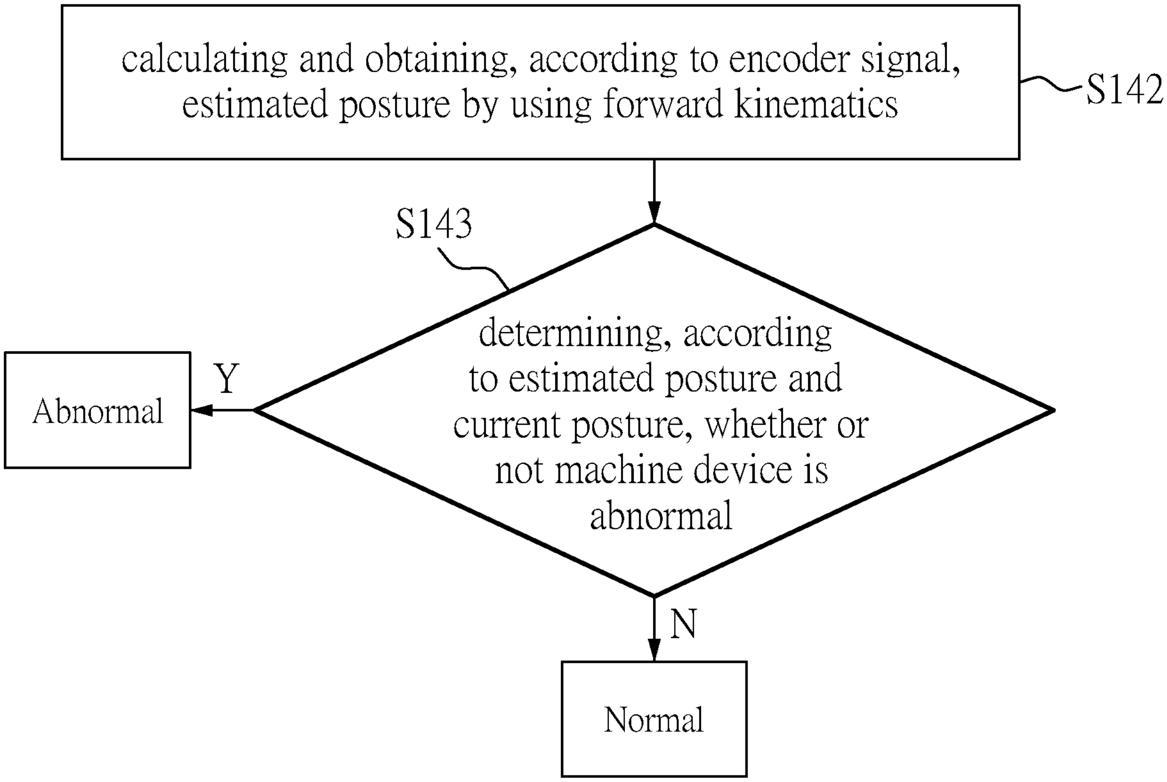
FIG. 5 is a second flowchart for step S14.

However, in addition to the above-mentioned determination method through inverse kinematics, one embodiment of the present disclosure also provides a determination method through forward kinematics. Reference is made to FIG. 5, which is a second detailed flowchart of step S14.

As shown in FIG. 5, step S14 can include the following steps:

Step S142: calculating and obtaining, according to the encoder signal, an estimated posture by using forward kinematics.

Step S143: determining, according to the estimated posture and the current posture, whether or not the machine device is abnormal.

If the machine device 10 is the serial robot, the estimated posture can be obtained from the encoder signals through forward kinematics by performing the above steps S142 and S143, and the estimated posture is then compared with the current posture $(T_E^B)$.

The transformation methods involving forward kinematics, the motor posture, and the motor encoder signals are known to those skilled in the art, and thus the details will not be repeated hereinafter.

Figure 6:
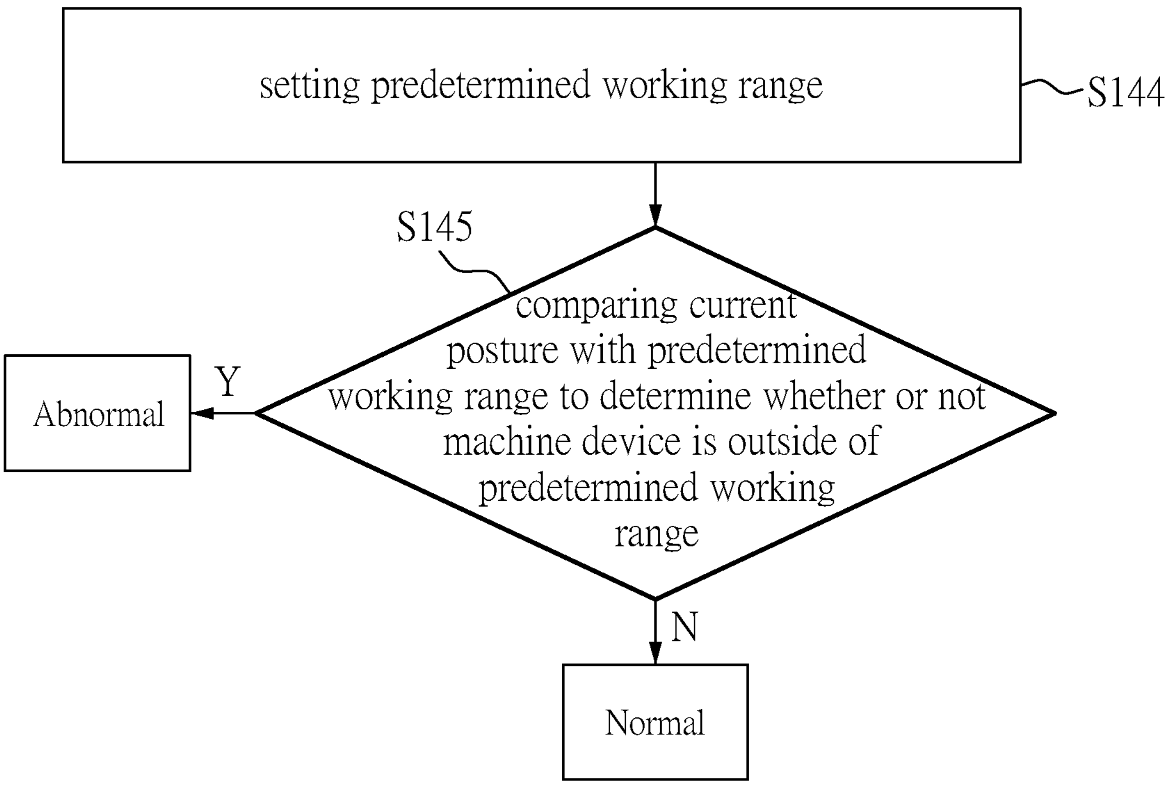
FIG. 6 is a third flowchart for step S14.

Reference is made to FIG. 6, which is a third detailed flowchart of step S14. In addition to the above-mentioned method of determining whether or not the machine device is abnormal, step S14 may further include the following steps:

Step S144: setting a predetermined working range.

Step S145: comparing the current posture with a predetermined working range to determine whether or not the machine device is outside of the predetermined working range.

It should be noted that the inspection mechanisms in FIGS. 4 and 5 mainly compare the current posture captured from the image with the posture measured by the motor encoder to determine whether or not there is any discrepancy, so as to determine whether an abnormal situation has occurred. However, such inspection mechanisms are incapable of completely ensuring that the machine device (or the surgical instrument 106) is still within a reasonable and proper working range. For this reason, the present disclosure further provides another inspection mechanism to ensure that the machine device (or the surgical instrument 106) is still operating within a reasonable working space.

Figure 7:
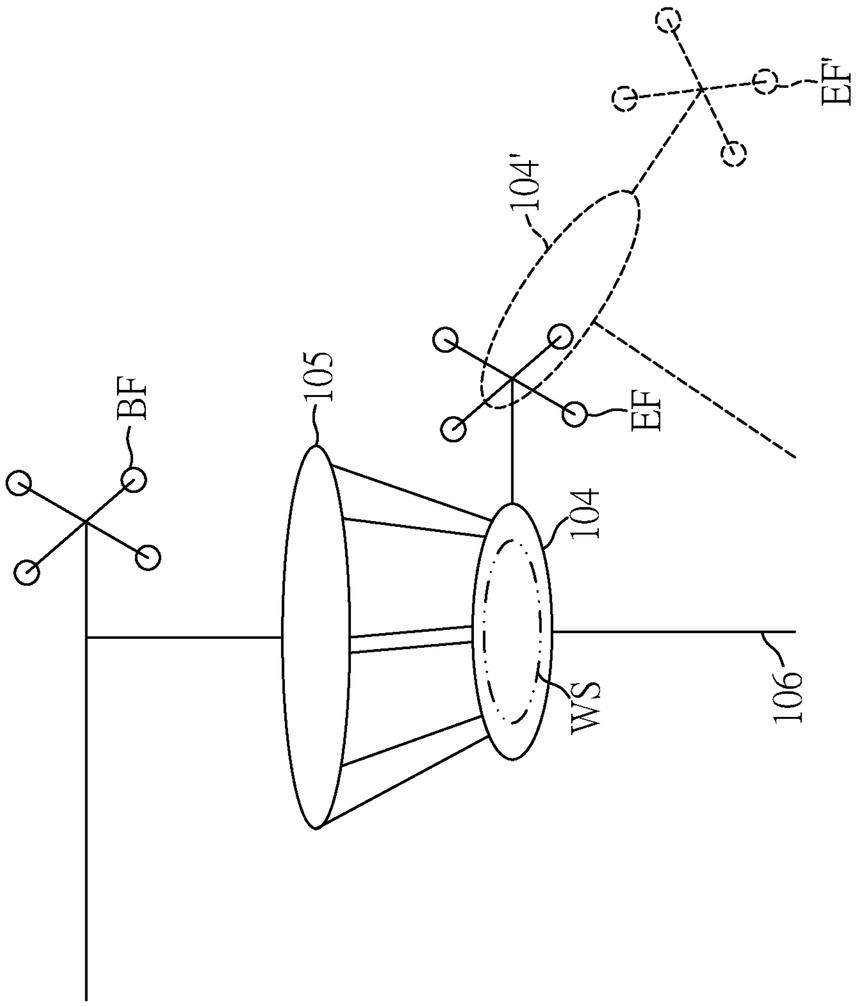
FIG. 7 is a schematic diagram showing a comparison between a current posture and a predetermined working range described in step S14.

Reference is made to FIG. 7, which is a schematic diagram showing a comparison between the current posture and the predetermined working range described in step S14. In this step, a predetermined working range WS can be set for one or more of the mobile platform 104, the base platform 105, and the surgical instrument 106. For example, as shown in FIG. 7, positions which may be reached by all mechanism parts of the machine device are first determined, those positions constitute a range, and this range is defined as a total working space. Next, the predetermined working range WS is set in the total working space for the mobile platform 104 according to practical requirements, in which the setting is performed by taking the base platform 105 as a reference to find a reasonable working range of the mobile platform 104, and a size and a position of the predetermined working range WS is further set, where the predetermined working range WS can be a two-dimensional space or a three-dimensional space. During the determination, for example, it is determined whether or not a center point of the mobile platform 104 is outside of the predetermined working range WS.

Taking FIG. 7 as an example, if it is detected that the first marker EF' is located at a position shown in FIG. 7, it can be known that the position of the mobile platform 104' is tilted to one side as shown and obviously exceeds the predetermined working range WS; this information then can be used to determine that the machine device 10 is abnormal. Such abnormality may be caused by detachment of the reference marker BF or the first marker EF, serious deformation of the robot, or abnormality of the image capturing device 12. For example, for a condition where the robot lunges abnormally and moves outside of the predetermined working range WS, although the inspection mechanisms in FIGS. 4 and 5 may have failed to detect such abnormality, it can be detected and warned by the inspection mechanism in FIG. 6.

Reference is made to FIG. 3, in response to determining that the machine device 10 is abnormal in step S14, the inspection method proceeds to step S15: generating a warning and a stop command to stop the machine device.

In this step, when an abnormality is detected, a warning can be given in various ways (for example, through a warning light, a horn, or an abnormal message displayed on the display device 16), and at the same time, movement of the robotic arm is stopped to ensure safety.

In response to determining that the machine device 10 is normal in step S14, the inspection method proceeds to step S16: calculating and generating a control command for the machine device according to the current posture and a target posture.

Step S17: controlling the motors by the control command to drive the machine device to transform to the target posture.

In steps S16 and S17, the control command to be executed by the machine device 10 at a next predetermined time point can be calculated and obtained by using the orientations of the reference marker BF and the first marker EF. That is to say, depending on the current posture of the machine device 10, the processing device 14 can set the target posture as a posture of the machine device 10 at which the surgical instrument 106 can advance along the surgical path 60 and the virtual axis 61, thereby assisting the user for moving steadily along the surgical path 60.

Figure 8:
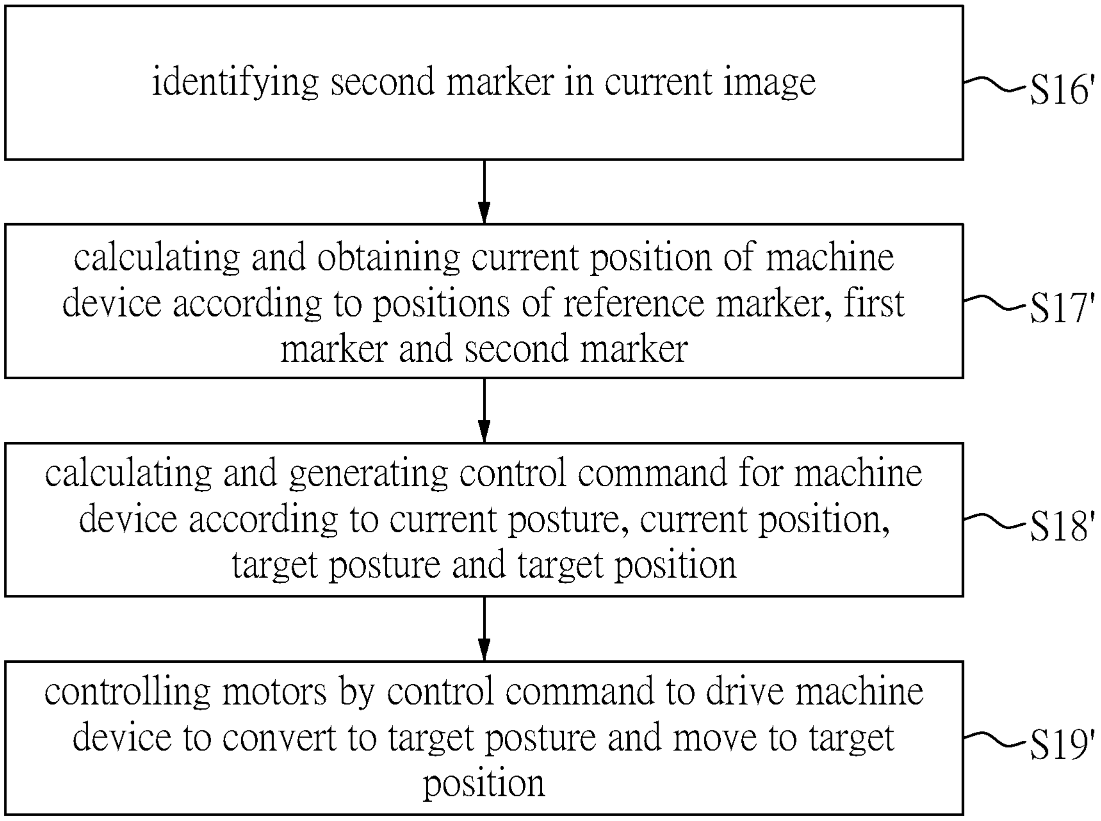
FIG. 8 is another flowchart of the machine posture inspection method according to one embodiment of the present disclosure.

FIG. 8 is another flowchart of the machine posture inspection method according to one embodiment of the present disclosure. Reference is made to FIG. 8, in one embodiment of the present disclosure, the inspection method can further include the following steps:

Step S16': identifying a second marker in the current image. The second marker FF is associated with the target working region, that is, the surgical site 2.

Step S17': calculating and obtaining a current position of the machine device according to the positions of the reference marker, the first marker and the second marker.

Step S18': calculating and generating the control command for the machine device according to the current posture, the current position, the target posture and the target position.

Step S19': controlling the motors by the control command to drive the machine device to convert to the target posture and move to the target position.

Similarly, in the above steps of FIG. 8, the positions and orientations of the reference marker BF, the first marker EF and the second marker FF can be used to calculate and generate the control command which is to be executed by the machine device 10 at a next predetermined time point. That is to say, depending on the current posture and the current position of the machine device 10, the processing device 14 can set the target posture and the target position as a posture and a position of the machine device 10 at which the surgical instrument 106 can advance along the surgical path 60 and the virtual axis 61, thereby assisting the user for moving steadily along the surgical path 60.

Beneficial Effects of the Embodiments

In conclusion, in the machine posture inspection method and machine posture inspection system provided by the present disclosure, a 3D image capturing device and a motor encoder are utilized to detect and obtain a posture of the machine device and a motor posture, which are compared with each other to ensure that the posture and movement of the machine device is normal. When an abnormality is detected, a warning is issued and the machine device is stopped to ensure system safety.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for determining an abnormality of a machine posture, comprising:

configuring an image capturing device to capture a current image of a region where a machine device is located; and configuring a processing device to:

identify a reference marker and a first marker associated with the machine device in the current image;

calculate and obtain a current posture of the machine device according to the reference marker and the first marker;

configure at least one motor encoder to measure an encoder signal associated with at least one motor; and determine, according to the current posture and the encoder signal, whether or not the machine device is abnormal;

wherein abnormalities of the machine device selectively include robot mechanism abnormalities, motor abnormalities, encoder abnormalities, and marker falling, wherein the step of determining whether or not the machine device is abnormal further includes:

calculating and obtaining, according to the current posture, an estimated encoder position of the at least one motor by using inverse kinematics; and comparing the estimated encoder position and the encoder signal of the at least one motor, so as to determine whether or not the machine device is abnormal;

wherein the at least one motor and a ball screw form a linear brake, the estimated encoder position is an estimated elongation of the brake shaft, the encoder signal is an actual elongation of the brake shaft, and the estimated elongation and the actual elongation of the brake shaft are compared to determine whether or not the machine device is abnormal.

2. The method according to claim 1, further comprising: configuring the processing device to:

calculate and generate a control command for the machine device according to the current posture and a target posture; and control the at least one motor by the control command to drive the machine device to move to the target posture.

3. The method according to claim 2, further comprising: configuring the processing device to:

identify a second marker in the current image, wherein the second marker is associated with a target work region;

calculate and obtain a current position of the mechanical device according to the positions of the reference marker, the first marker and the second marker;

calculate and generate the control command for the machine device according to the current posture, the current position, the target posture and a target position; and control the at least one motor by the control command to drive the machine device to move to the target posture and move toward the target position.

4. The method according to claim 3, further comprising: configuring the processing device to:

compare the current posture with a predetermined working range to determine whether or not the machine device is outside of the predetermined working range; and in response to the machine device being outside of the predetermined working range, determine that the machine device is abnormal.

5. The method according to claim 4, wherein the machine device includes a base platform and a mobile platform with a plurality of degrees of freedom relative to the base platform, the mobile platform is driven by the at least one motor, the first marker is arranged at the base platform of the machine device, and the second marker is arranged at the mobile platform of the machine device.

6. A system for determining an abnormality of a machine posture, comprising:

a machine device including at least one motor and at least one motor encoder;

an image capturing device configured to capture a current image of a region where the machine device is located; and a processing device electrically connected to the image capturing device and the machine device, wherein the processing device is configured to:

identify a reference marker and a first marker associated with the machine device in the current image;

calculate and obtain a current posture of the machine device according to the reference marker and the first marker;

measure an encoder signal associated with the at least one motor through the at least one motor encoder; and determine, according to the current posture and the encoder signal, whether or not the machine device is abnormal;

wherein abnormalities of the machine device selectively include robot mechanism abnormalities, motor abnormalities, encoder abnormalities, and marker falling, wherein the step of determining whether or not the machine device is abnormal further includes:

calculating and obtaining, according to the current posture, an estimated encoder position of the at least one motor by using inverse kinematics; and comparing the estimated encoder position and the encoder signal of the at least one motor, so as to determine whether or not the machine device is abnormal;

wherein the at least one motor and a ball screw form a linear brake, the estimated encoder position is an estimated elongation of the brake shaft, the encoder signal is an actual elongation of the brake shaft, and the estimated elongation and the actual elongation of the brake shaft are compared to determine whether or not the machine device is abnormal.

7. The system according to claim 6, wherein the processing device is further configured to:

calculate and generate a control command for the machine device according to the current posture and a target posture; and control the at least one motor by the control command to drive the machine device to move to the target posture.

8. The system according to claim 7, wherein the processing device is further configured to:

identify a second marker in the current image, wherein the second marker is associated with a target work region;

calculate and obtain a current position of the mechanical device according to the positions of the reference marker, the first marker and the second marker;

calculate and generate the control command for the machine device according to the current posture, the current position, the target posture and a target position; and control the at least one motor by the control command to drive the machine device to move to the target posture and move toward the target position.

9. The system according to claim 8, wherein the processing device is further configured to:

compare the current posture with a predetermined working range to determine whether or not the machine device is outside of the predetermined working range; and in response to the machine device being outside of the predetermined working range, determine that the machine device is abnormal.

10. The system according to claim 9, wherein the machine device includes a base platform and a mobile platform with a plurality of degrees of freedom relative to the base platform, the mobile platform is driven by the at least one motor, the first marker is arranged at the base platform of the machine device, and the second marker is arranged at the mobile platform of the machine device.

* * * * *